United States Patent [19]
Alfano

[11] Patent Number: 5,413,108
[45] Date of Patent: May 9, 1995

[54] METHOD AND APPARATUS FOR MAPPING A TISSUE SAMPLE FOR AND DISTINGUISHING DIFFERENT REGIONS THEREOF BASED ON LUMINESCENCE MEASUREMENTS OF CANCER-INDICATIVE NATIVE FLUOROPHOR

[75] Inventor: Robert R. Alfano, Bronx, N.Y.

[73] Assignee: The Research Foundation of City College of New York, New York, N.Y.

[21] Appl. No.: 51,014

[22] Filed: Apr. 21, 1993

[51] Int. Cl.$^6$ .............................................. A61B 6/00
[52] U.S. Cl. ................................................. 128/665
[58] Field of Search ............... 128/632–634, 128/664–665

[56] References Cited

U.S. PATENT DOCUMENTS

| | | |
|---|---|---|
| 4,930,516 | 6/1990 | Alfano et al. |
| 5,042,494 | 8/1991 | Alfano . |
| 5,131,398 | 7/1992 | Alfano et al. |
| 5,199,431 | 4/1993 | Kittrell et al. ................. 128/665 |

FOREIGN PATENT DOCUMENTS 2-22331 7/1983 Japan .

OTHER PUBLICATIONS

Eyre, D. R., Science 207:1315–1322 (1980).
Gross, J., Harvey Lectures, 68:351–432 (1973).
Ross, R. et al., Sci. Amer., 224(6), 44–52 (1971).
Sandberg, L. B., Int. Rev. Connect. Tissue Res., 7:159–210 (1976).
Alfano, R. R. et al., IEEE J. of Quantum Electronics, vol. QE-20, No. 12 1507–1511 (1984).
Alfano, R. R. et al., IEEE J. of Quantum Electronics, vol. QE-23, No. 10 1806–1811 (1987).

*Primary Examiner*—Ruth S. Smith
*Attorney, Agent, or Firm*—Kriegsman & Kriegsman

[57] ABSTRACT

A method and apparatus for examining a two-dimensional region of a tissue sample. This is accomplished, according to one embodiment of the invention, by illuminating, i.e., exciting, the two-dimensional tissue sample with light at a first wavelength. The resultant fluorescence is then measured at an emission wavelength as a function of location within the two-dimensional tissue sample. The two-dimensional tissue sample is then illuminated again with light at a second wavelength, and the resultant fluorescence is measured at the same emission wavelength. The two excitation wavelengths and the emission wavelength are appropriately chosen so that the ratio or difference of fluorescence intensities at the emission wavelength is indicative of the carcinomatous condition of the tissue. A value, such as a ratio or difference, of the respective intensity measurements obtained at each location of the tissue sample is then calculated. These values are then compared to appropriate standards, and the results are depicted in the form of a map. The invention is premised on the discovery that certain native, commonly-occuring molecules, such as collagen, NAD+/NADH, NADP+/NADPH, flavins, tryptophan, and elastin, fluoresce differently in cancerous tissue than in non-cancerous tissue.

8 Claims, 8 Drawing Sheets

METHOD AND APPARATUS FOR MAPPING A TISSUE SAMPLE FOR AND DISTINGUISHING DIFFERENT REGIONS THEREOF BASED ON LUMINESCENCE MEASUREMENTS OF CANCER-INDICATIVE NATIVE FLUOROPHOR

BACKGROUND OF THE INVENTION

The present invention relates generally to methods and apparatuses for detecting cancer and more particularly to a method and apparatus for mapping a tissue sample and for distinguishing different regions thereof based on luminescence measurements of cancer-indicative native fluorophors.

Because a sufficiently effective method has not yet been developed to prevent cancer, cancer research has focused on the most effective ways to treat cancer. As different as the various forms of treatment have been—ranging from excision to radiation to chemotherapy—all treatments have relied on one crucial step, the detection of cancerous tissue. The importance of detection cannot be stressed enough. Early detection not only indicates the presence of a cancer but also may give an indication as to where the cancer originated and what type of treatment will be the most safe and effective. In addition to being used to detect cancer early, detection methods may also be used to determine whether treatment methods have been successful in eradicating cancer from a patient.

At present, methods for detecting cancer have relied primarily on the use of X-rays, nuclear magnetic resonance, nuclear radiation or invasive methods based on chemical laboratory analysis and biopsy.

In U.S. Pat. No. 5,042,494, which is incorporated hereinto by reference, there is disclosed a method and apparatus for detecting the presence of cancerous tissue using native visible luminescence. The tissue to be examined is excited with a beam of light that causes the tissue to fluoresce over a spectrum of wavelengths. The intensity at which the excited tissue fluoresces can be measured either over a spectrum or at a predetermined number of preselected wavelengths. By determining the wavelength(s) at which maximum intensity(ies) are attained for the tissue in question and by comparing these peak wavelengths, either visually or electronically, to the peak wavelength(s) derived from a known non-cancerous tissue, or by comparing the luminescence spectrum of the excited tissue with the luminescence spectrum of a known non-cancerous tissue and/or known cancerous tissue or the excitation spectra of the excited tissue with the excitation spectra of known cancerous and/or known non-cancerous tissue, one can determine the carcinomatoid status of the tissue in question.

In U.S. Pat. No. 5,131,398, which is also incorporated hereinto by reference, there is disclosed a method and apparatus for distinguishing cancerous tumors and tissue from benign tumors and tissue or normal tissue using native fluorescence. The tissue to be examined is excited with a beam of monochromatic light at 300 nanometers (nm). The intensity of the native fluorescence emitted from the tissue is measured at 340 and 440 nm. The ratio of the two intensities is then calculated and used as a basis for determining if the tissue is cancerous as opposed to benign or normal.

Other patents or publications of interest may include Photometrics CCD Newsbrief, Photometrics Ltd., Tuscon, Ariz. (December, 1992); Silicon-Detector Arrays Advance Medical Imaging, Laser Focus World, pp. 139-140 & 142-143 (March, 1993); and a paper entitled "Discrimination and Classification with Xybion Multispectral Video Systems," by Paul A. Frost, presented at the 19th International Congress on High-Speed Photography & Photonics, Cambridge, UK (Sep. 18, 1990), all of which are hereby incorporated by reference.

SUMMARY OF THE INVENTION

The present invention is premised on the discovery that certain native, commonly-occuring molecules, such as collagen, NAD+/NADH, NADP+-/NADPH, flavins, tryptophan, and elastin, fluoresce differently in cancerous tissue than in non-cancerous tissue. This discovery is exploited in the present invention by the provision of a method and apparatus for mapping a two-dimensional tissue sample so that regions thereof whose native fluorescence for one or more cancer-indicative fluorophors and different may be easily identified.

This is accomplished, according to one embodiment of the invention, by illuminating, i.e., exciting, the two-dimensional tissue sample with light at a first wavelength. The resultant fluorescence emitted over various areas of the tissue sample is then measured at an emission wavelength. The two-dimensional tissue sample is then illuminated again with light at a second wavelength, and the resultant fluorescence is measured at the same emission wavelength. The two excitation wavelengths and the emission wavelength are appropriately chosen so that the ratio or difference of fluorescence intensities at the emission wavelength is indicative of the carcinomatous condition of the tissue. A ratio or difference of the respective intensity measurements obtained over each area of the sample is then calculated. The ratios or differences for the respective areas are then compared to appropriate standards, and the results are depicted graphically in the form of a map.

Such a mapping system can be used to illustrate the relative spatial locations of malignant and non-malignant regions within a tissue sample and/or can be used to monitor known malignant regions within a tissue sample to determine the effectiveness of treatments administered thereto.

Objects, features and advantages of the present invention will be set forth in part in the description which follows, and in part will be obvious from the description or may be learned by practice of the invention. The objects, features and advantages of the present invention may be realized and attained by means of the instrumentalities and combinations particularly pointed out in the appended claims.

BRIEF DESCRIPTION OF THE DRAWINGS

The accompanying drawings, which are hereby incorporated into and constitute a part of this specification, illustrate the preferred embodiments of the invention and, together with the description, serve to explain the principles of the invention. In these drawings wherein like reference numerals represent like parts.

DETAILED DESCRIPTION OF PREFERRED EMBODIMENTS

Figure 1:
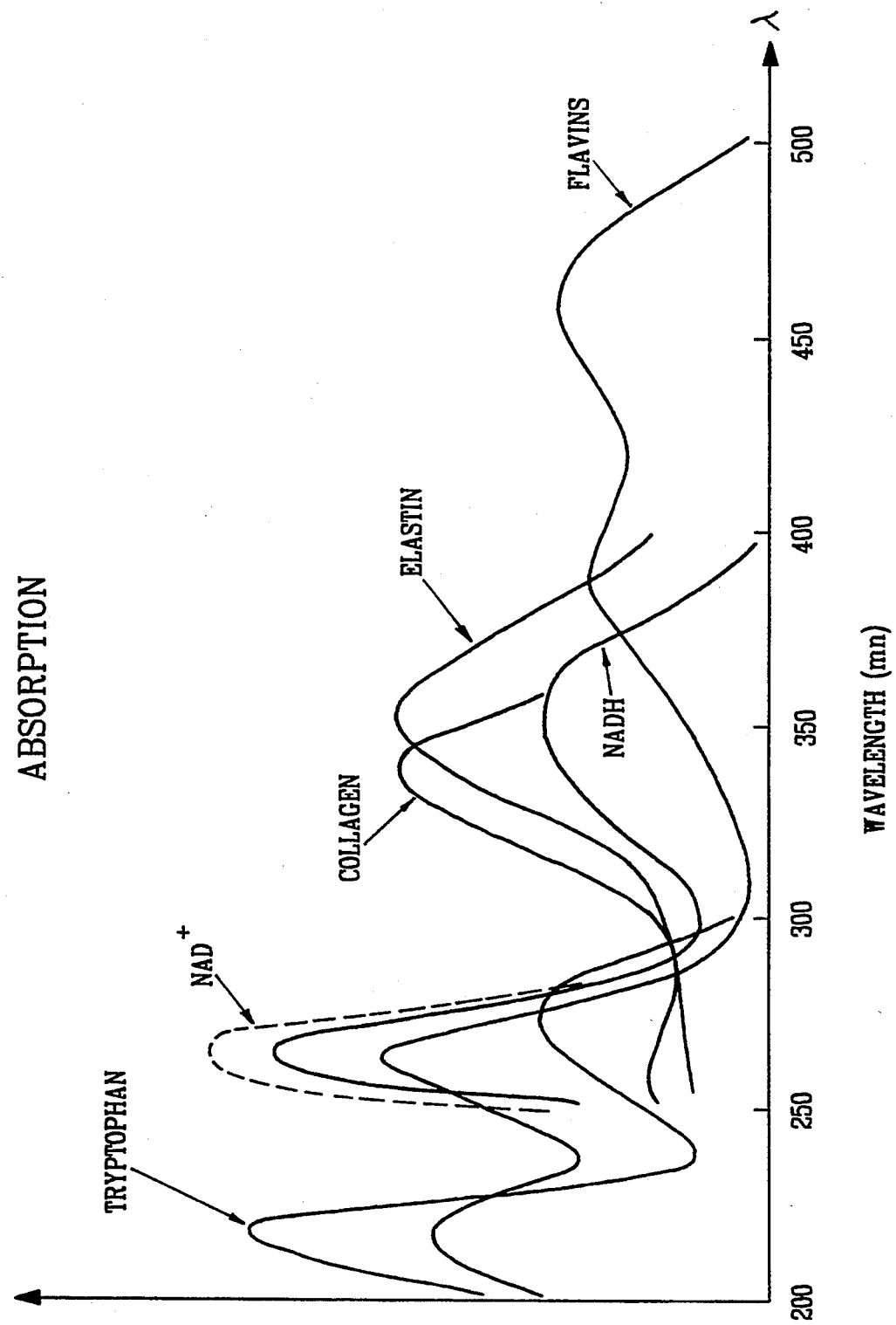
FIG. 1 graphically depicts the absorption spectra of certain native fluorophors which fluoresce differently in cancerous and non-cancerous tissues.
Figure 2:
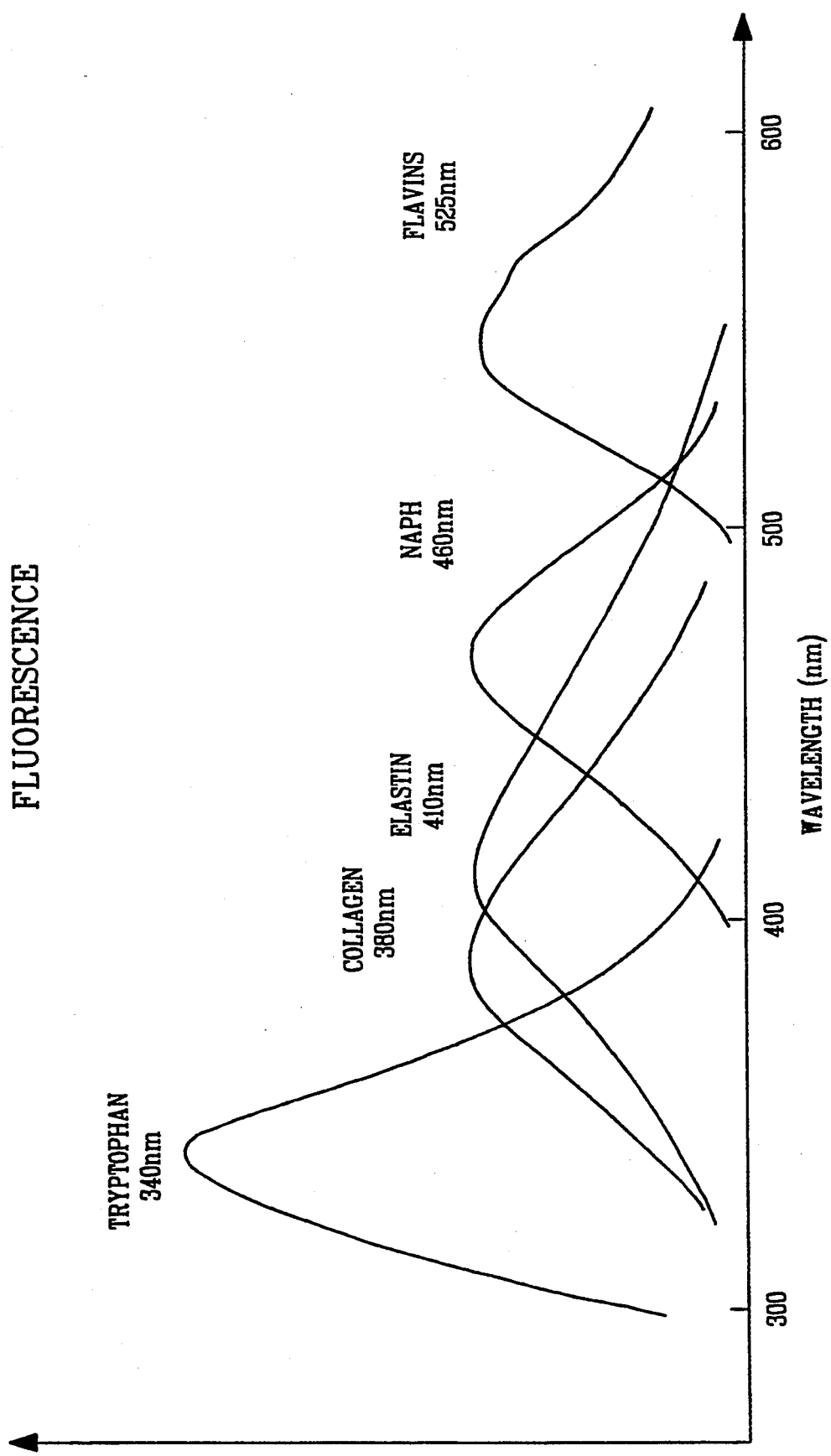
FIG. 2 graphically depicts the fluorescence spectra of certain native fluorophors which fluoresce differently in cancerous and non-cancerous tissues.

The theoretical underpinings for most cancer detection methods reliant on native luminescence measurements are as follows: Certain native fluorophors present in virtually all tissues, e.g. tryptophan, NADH, collagen, elastin, and flavins, have been shown to optically change in malignant and non-malignant states of tissue. The key absorption and fluorescence spectral features of these fluorophors are displayed in FIGS. 1 and 2. These fluorophors are among many others with similar properties from which a selection may be made. Changes in fluorescence patterns arise from a number of these fluorophors and the efficiency to emit and absorb light at a particular wavelength. Some of these molecules are likely involved in protein synthesis, electron transport chain and production of energy in the body, e.g. tryptophan, NADH, and flavins. Collagen, for example, is manufactured in the body to patch wounds and mend broken bones. Elastin protein fibers are manufactured in the body to give muscles strength. By monitoring some of these molecules, such as tryptophan, NAPH, and flavins, one can detect changes in the underlying metabolism, electron transport, and molecular activity in malignant and non-malignant states of tissues.

This type of "optical histology and pathology" spectral excitation imaging method depends on the absorption co-efficients of types of molecules, the number of molecules present and fluorescence yields of the material $= \sigma_i N_i \Phi_i$. For two excitation wavelengths ($\lambda_1$ and $\lambda_2$), the spectral signature fingerprint depends on:

$$\sim \Sigma \sigma_i(\lambda_1) N_i + \Sigma \sigma_i(\lambda_2) N_i \quad (1)$$

wherein $\sigma_i$ is the absorption cross-section and $N_i$ is the number of molecules, i. The emission at wavelength $\lambda_{Fi}$ depends on relative quantum yield, $\Phi_i$, (radiative ($k_r$) and nonradiative ($k_{nr}$) rates) from the selected pumped molecules:

$$I_F(\lambda_{Fi}) \sim \Sigma \Phi_i N_i \quad (2)$$

A simple example is to excite using two wavelengths ($\lambda_1$ and $\lambda_2$) and then to measure the fluorescence at one wavelength $\lambda_F$. This method can be made more complex by excitation at more than two wavelengths ($\lambda_1$, $\lambda_2$, $\lambda_3$) followed by measurement at other key molecules which emit at $\lambda_{F1}$, $\lambda_{F2}$, etc.

The method proposed is to use only two excitation wavelengths ($\lambda_1$ and $\lambda_2$) and to measure the fluorescence at one wavelength ($\lambda_F$) to give a map of the spatial region ($X_i$, $Y_i$). One is to measure the ratio of the fluorescence at $\lambda_F$ at space coordinate $X_i$, $Y_i$ for the relative excitation at two wavelengths $\lambda_1$ and $\lambda_2$:

$$\text{Spectral Ratio Map } (X_i, Y_i) = SRM = \frac{\{I_F(\lambda_F)ex(\lambda_1)at(X_i, Y_i)\}}{\{I_F(\lambda_F)ex(\lambda_2)at(X_i, Y_i)\}} \quad (3)$$

Figure 3:
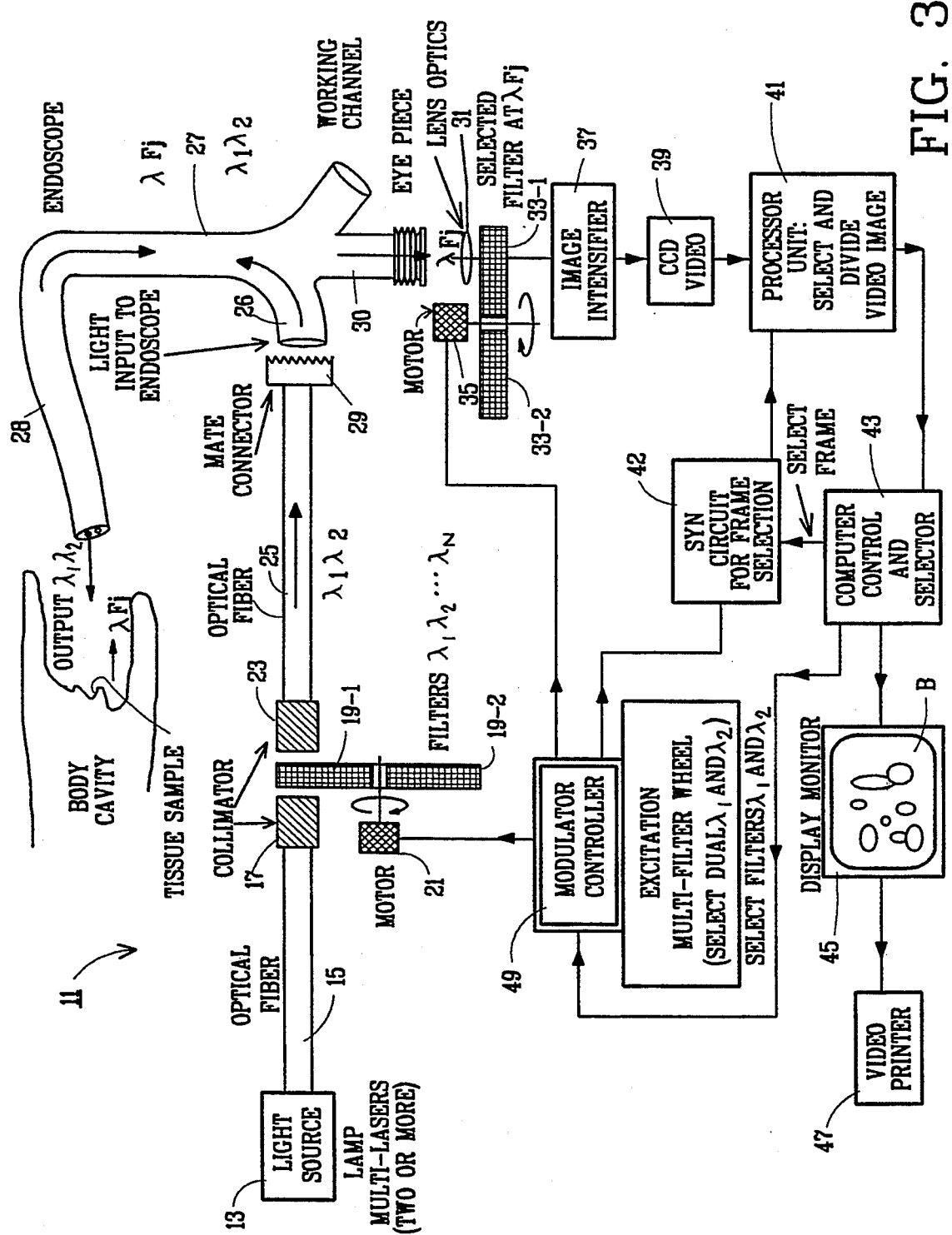
FIG. 3 is a schematic diagram of one embodiment of an apparatus constructed according to the teachings of the present invention for mapping a tissue sample in such a way as to identify regions thereof whose native fluorescence differs for use in detecting cancer.

Referring now to FIG. 3, there is schematically shown an apparatus constructed according to the teachings of the present invention for mapping a tissue sample so that regions thereof whose native fluorescence differ in a manner indicative of cancer may be identified, the apparatus being represented generally by reference numeral 11.

As can be seen, apparatus 11 includes a light source 13, which may be either a lamp/filter combination or two or more lasers. The light emitted from light source 13 is transmitted via an optical fiber 15 first through a collimator 17 and then through either one of a pair of filters 19-1 and 19-2 to produce light of excitation wavelengths $\lambda_1$ and $\lambda_2$, respectively. Filters 19-1 and 19-2 are preferably mounted on a rotatable filter wheel (not shown), the angular orientation of which is driven by a motor 21. The light passed through either filter 19-1 or 19-2 is then passed through a second collimator 23 and is transmitted through a second optical fiber 25 to a first leg 26 of an endoscope 27. Fiber 25 and first leg 26 of endoscope 27 are coupled together by a mate connector 29. Endoscope 27 transmits the light through a second leg 28 to the tissue sample to be examined. It should be noted that, when the excitation wavelength is below 320 m, the endoscope optical fiber should be quartz.

As can be seen, in the embodiment shown, the tissue sample is located within a body cavity of a patient, thereby permitting in vivo examination.

The resultant fluorescence emitted from the tissue sample is then transmitted back through second leg 28 of endoscope 27 and out a third leg 30, where it is focused by optics 31 and then passed through either one of a pair of filters 33-1 and 33-2 (each selective for fluorescent light of a desired emission wavelength). Filters 33-1 and 33-2 are mounted on a second rotatable filter wheel (not shown), the rotation of which is driven by a motor 35. The light passed through either filter 33-1 or 33-2 is then intensified by an image intensifier 37 and detected by a CCD video 39, preferably having a spatial resolution of approximately 25 microns (2-3 pixels). The signals from the CCD video 39 corresponding to various areas within the tissue sample being examined are processed and synchronized for use in making a map by a processor unit 41, syn circuit 42 and computer 43. The resultant map is then displayed on a monitor 45 and video printer 47. A modulator controller 49, which is controlled by computer 43, is used to control the operation of motors 21 and 35.

As can readily be appreciated, apparatus 11 may be used in either or both of the following ways to take luminescence measurements of the tissue sample: (1) Using filters 19-1 and 19-2 successively, the tissue sample may be excited with light of two different wavelengths, with the resultant fluorescence being detected at a constant emission wavelength using either one of filters 33-1 or 33-2; or (2) Using either filter 19-1 or filter 19-2, the tissue sample may be excited with light of a constant wavelength, with the resultant fluorescence being passed successively through filters 33-1 and 33-2 for measurement at a pair of different wavelengths. In either case, the ratios or differences of the two luminescence measurements for the various areas of the region are then calculated and used to generate a map showing regions of varying native fluorescence. As can readily be appreciated, there are myriad different ways in which such information can be conveyed in a map. For example, in the map shown on monitor 45 of FIG. 3, the different colored bounded regions (i.e., the white, gray and black ovals and circles) are used to represent the various regions of the tissue sample whose native fluorescence ratio (or difference) differs from that of the remainder of the tissue sample (represented by the monolithic background B) and exceeds pre-set threshhold values.

As can readily be appreciated, filters 19-1 and 19-2 and filters 33-1 and 33-2 should be appropriately selected so that the fluorescence emitted from the tissue sample will be indicative of whether the tissue is cancerous as opposed to non-cancerous. This may be done by exciting the different fluorophors at various excitation wavelengths to show changes in malignant and nonmaligant regions of tissue, e.g., NADH at 350 nm and tryptophan at 300 nm with fluorescence measured at 460 nm. Other examples are to excite NAPH, elastin, and collagen at 340 nm and flavins at 420 nm and measure the fluorescence emission ratio map at 480 nm in space. A further example is to excite collagen at 320 nm and NAPH at 360 nm and measure the emission at 460 nm. These possible excitations will give a ratio intensity map for the two wavelengths of excitation for a wavelength $\lambda_F$ given fluorescence emission.

Figure 5A:
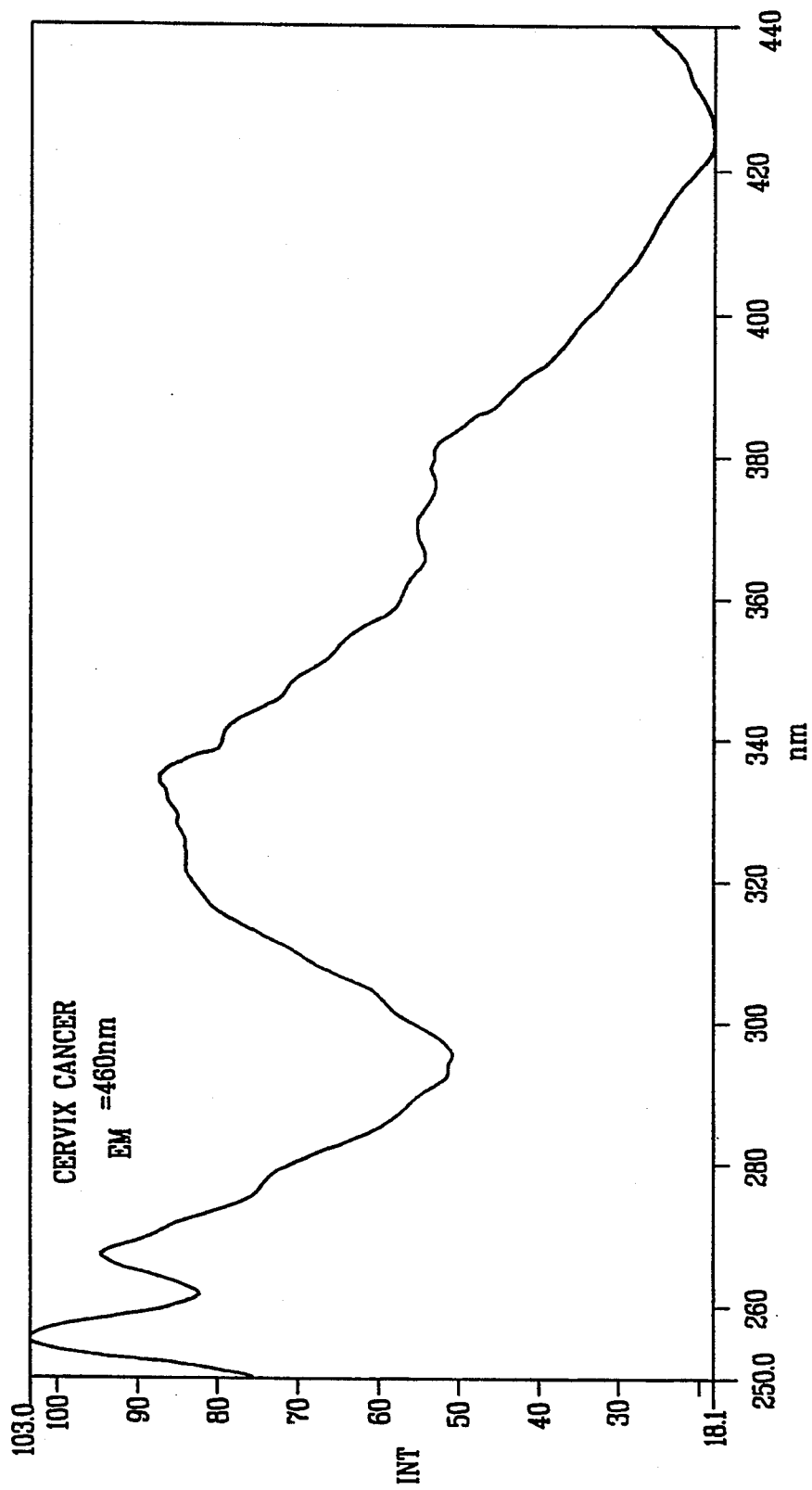
FIGS. 5(a) and 5(b) graphically depict excitation spectra measured at 460 nm for malignant cervical tissue and normal cervical tissue, respectively.
Figure 5B:
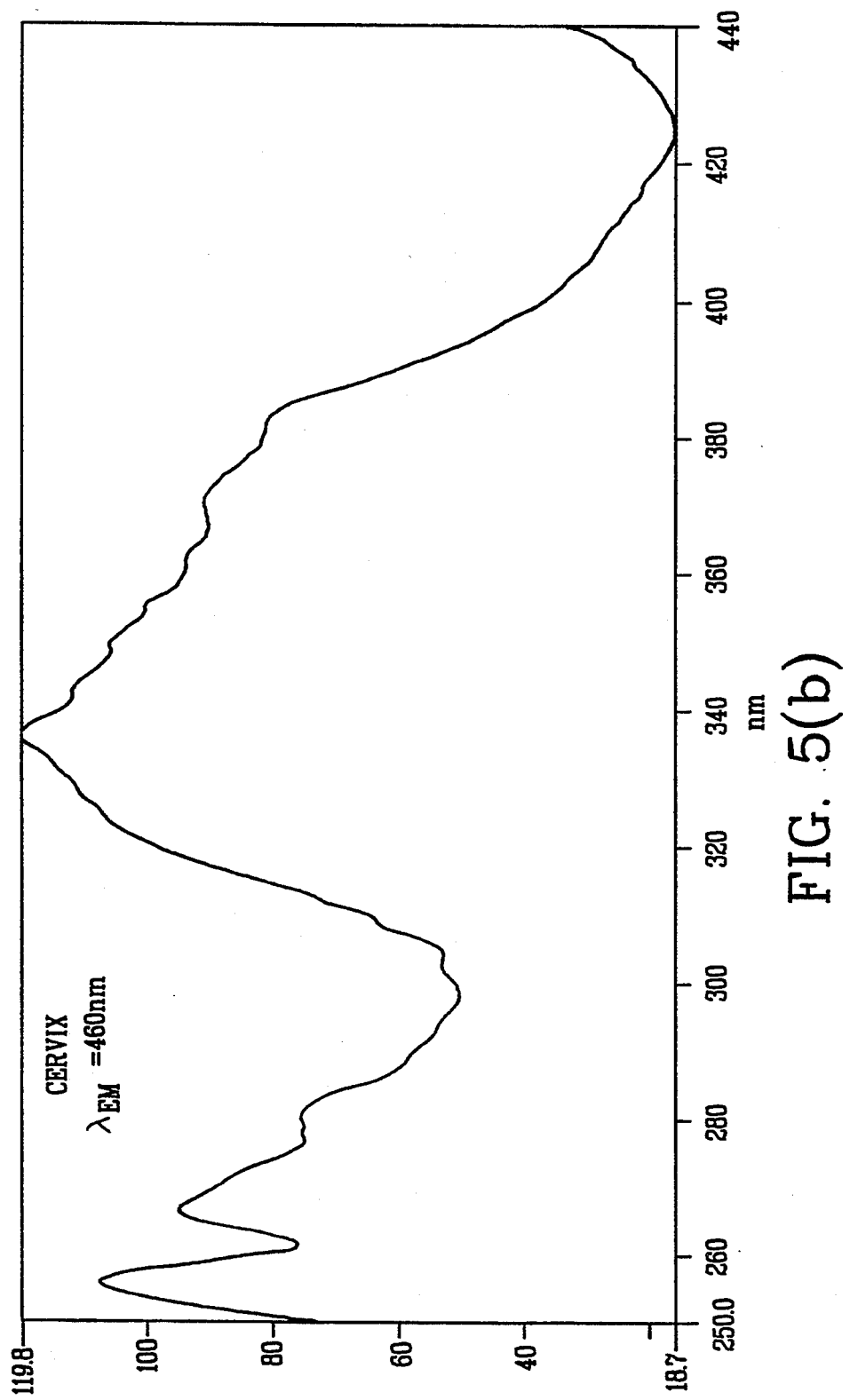
Figure 6:
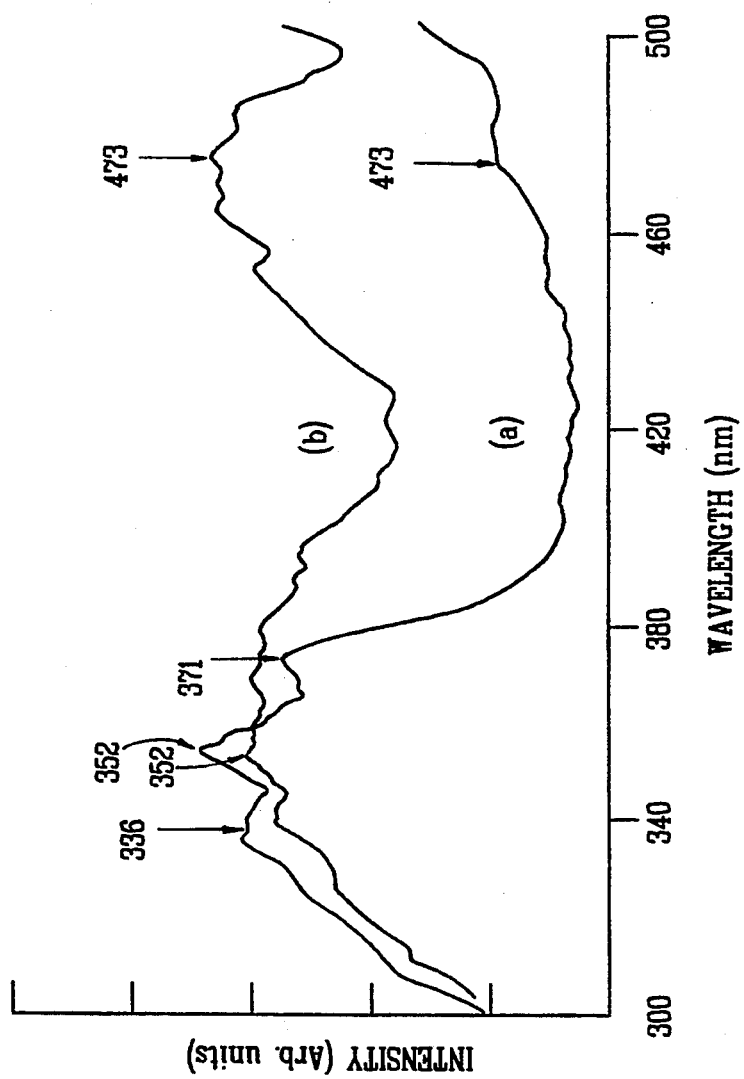
FIG. 6 graphically depicts excitation spectra measured at 520 nm for human normal breast tissue and human tumor breast tissue.

Referring generally to FIGS. 4 through 6, there are shown various examples of excitation spectra of tissues showing the possible pair of excitation wavelengths ($\lambda_1$ and $\lambda_2$) and fluorescence emission ($\lambda_F$) which can be selected from example test data for spectral mapping of malignant and non-malignant GYN and breast tissues using the instrument shown in FIG. 3.

Figure 4A:
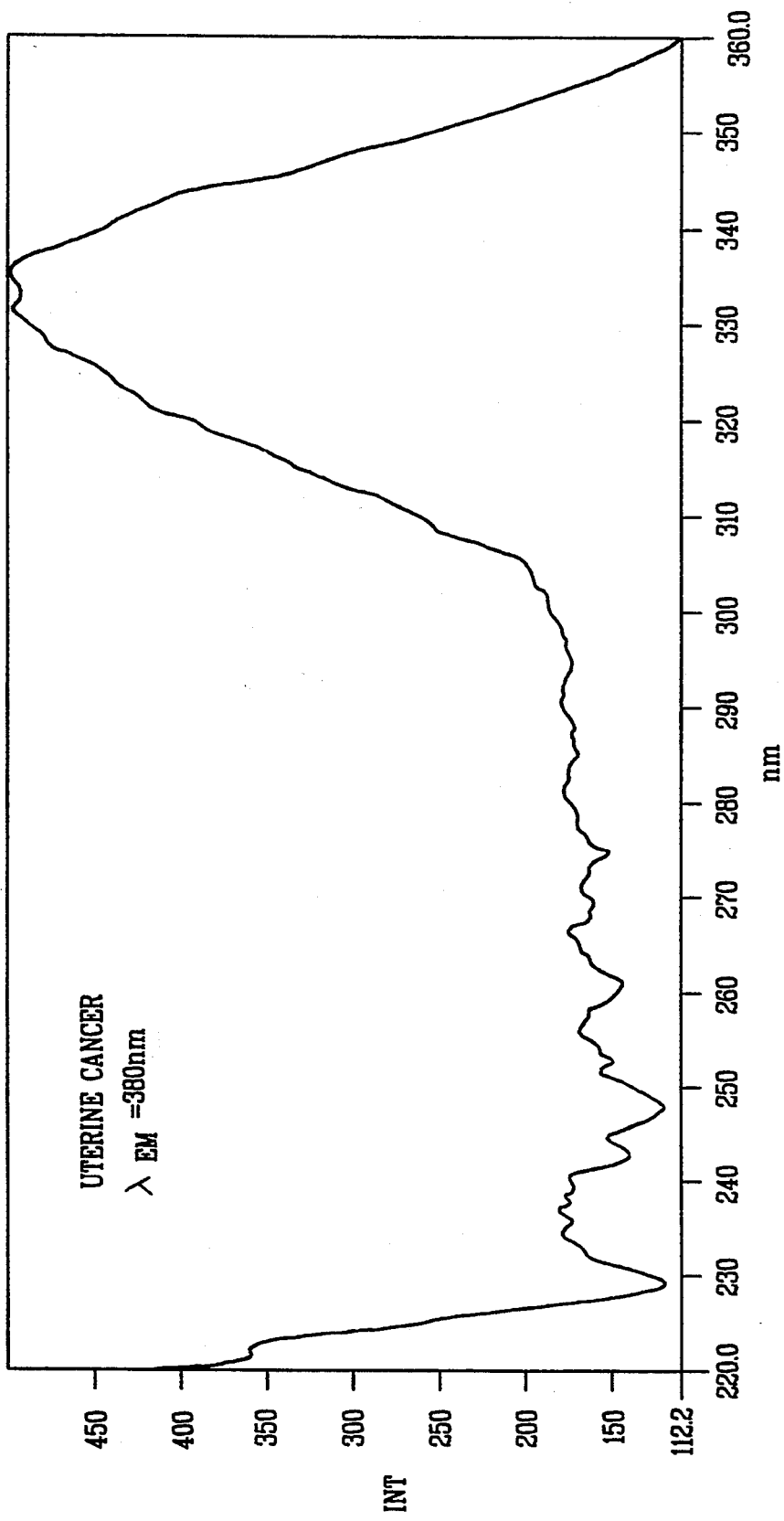
FIGS. 4(a) and 4(b) graphically depict excitation spectra measured at 380 nm for malignant cervical tissue and non-malignant myometrium tissue, respectively.
Figure 4B:
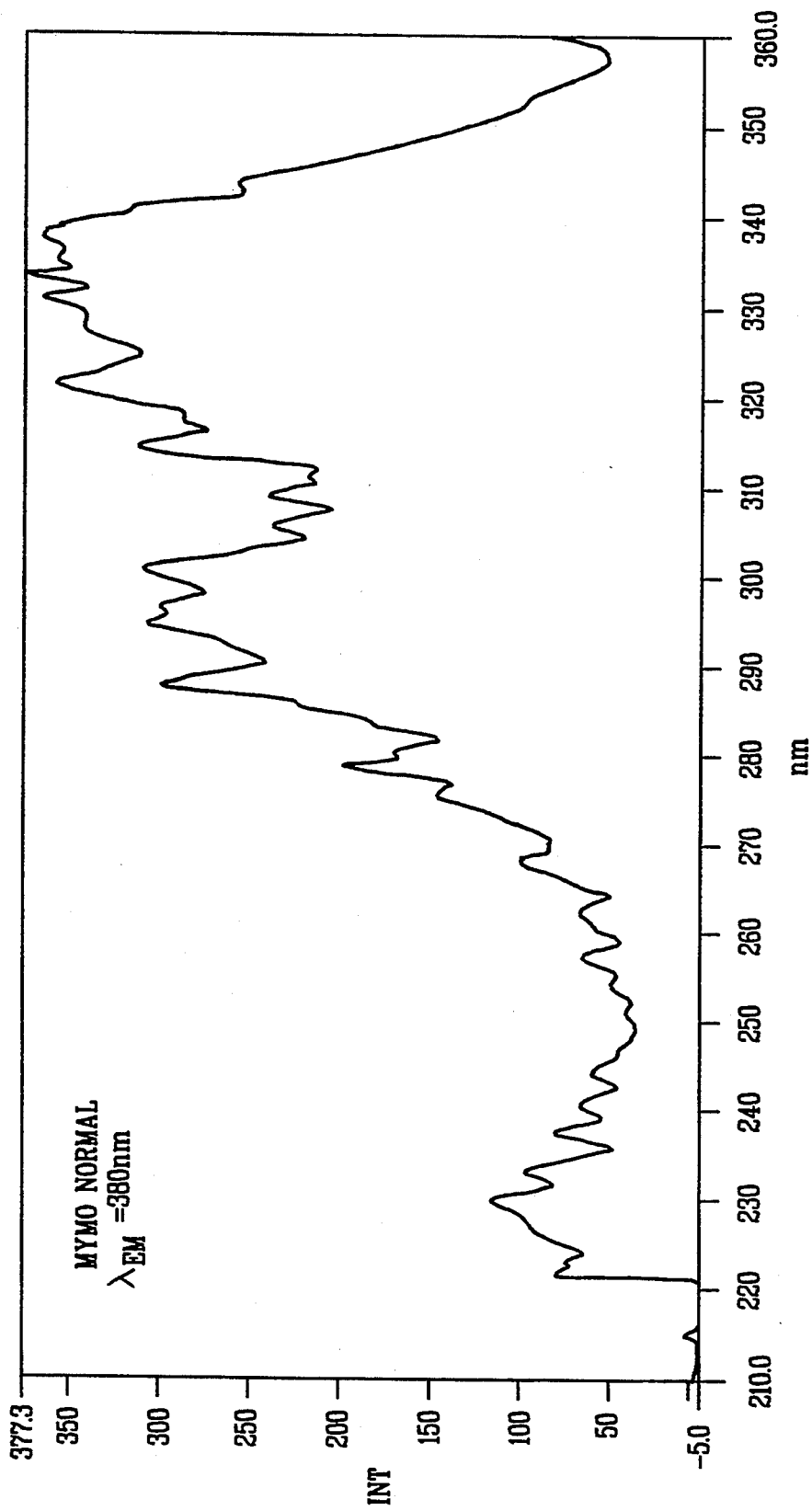

Referring now specifically to FIGS. 4(a) and 4(b), excitation spectra are shown for malignant and nonmalignant cervical and myometrium tissues, respectively. The optimum wavelengths to observe changes in these tissues are excitation wavelengths of about $\lambda_1 = 300$ nm and $\lambda_2 = 340$ nm, with an emission wavelength of about $\lambda_F = 380$ nm. Wavelength $\lambda_1$ excites protein (e.g. tryptophan), and wavelength $\lambda_2$ excites NADH, elastin and collagen.

Referring now specifically to FIGS. 5(a) and 5(b), excitation spectra are shown for cervical cancer tissue and normal tissue, respectively. As can be seen, the optimum excitation wavelengths are about $\lambda_1 = 340$ nm and $\lambda_2 = 380$ nm, with an emission wavelength of about $\lambda_F = 460$ nm. Wavelength $\lambda_1$ excites NADH, collagen, and elastin, and wavelength $\lambda_2$ excites NADH, and flavins.

Referring now specifically to FIGS. 6(a) and 6(b), excitation spectra are shown for human breast tissue and human tumor breast tissue, respectively. As can be seen, the optimum wavelengths to see change in breast cancer and normal tissue are excitation wavelengths of about $\lambda_1 = 340$ nm and $\lambda_2 = 460$ nm, with emission detected at a wavelength of $\lambda_F = 520$ nm. Wavelength $\lambda_1$ excites NADH, elastin and collagen, and wavelength $\lambda_2$ excites flavins.

As can readily be appreciated, because the fluorescence and absorption bands for the above-mentioned fluorophors are broad (see FIGS. 1 and 2), the above-noted wavelengths are only examples of suitable wavelengths, with other wavelengths in the respective absorption and fluorescence bands of the fluorophors also being suitable.

The embodiments of the present invention are intended to be merely exemplary and those skilled in the art shall be able to make numerous variations and modifications to it without departing from the spirit of the present invention. For example, it is expected that, in addition to being useful in the detection of cancer, the above-described method and apparatus may be also be used to detect other disease states for which naturally occurring fluorophors fluoresce differently in normal tissue than in diseased tissue. All such variations and modifications are intended to be within the scope of the present invention as defined in the appended claims.

What is claimed is:

1. A method of examining a two-dimensional tissue sample comprising the steps of:
   a) exciting the two-dimensional tissue sample with light at a first wavelength, whereby native fluorescence is emitted therefrom;
   b) measuring the intensity of the native fluorescence emitted from the two-dimensional region at a second wavelength as a function of location within the two-dimensional tissue sample;
   c) exciting the two-dimensional tissue sample with light at a third wavelength, whereby native fluorescence is emitted therefrom;
   d) measuring the intensity of the native fluorescence emitted from the two-dimensional tissue sample at said second wavelength as a function of location within the two-dimensional tissue sample;
   e) said first and said third wavelengths being such that the difference of intensities of the resultant native fluorescence measured at said second wavelength is indicative of the carcinomatous condition of the tissue sample;
   f) determining the difference of intensities measured at said second wavelength to obtain a value for each location within the two-dimensional tissue sample; and
   g) generating a map using said values.

2. A method of examining a two-dimensional tissue sample comprising the steps of:
   a) exciting the two-dimensional tissue sample with light at a first wavelength, whereby native fluorescence is emitted therefrom;
   b) measuring the intensity of the native fluorescence emitted from the two-dimensional region at a second wavelength as a function of location within the two-dimensional tissue sample;
   c) exciting the two-dimensional tissue sample with light at a third wavelength, whereby native fluorescence is emitted therefrom;
   d) measuring the intensity of the native fluorescence emitted from the two-dimensional tissue sample at said second wavelength as a function of location within the two-dimensional tissue sample;
   e) said first and said third wavelengths being such that the ratio of intensities of the resultant native fluorescence measured at said second wavelength is indicative of the carcinomatous condition of the tissue sample;
   f) determining the ratio of intensities measured at said second wavelength to obtain a value for each location within the two-dimensional tissue sample; and
   g) generating a map using said values.

3. The method as claimed in claim 2 wherein said first wavelength is 300 nm, said second wavelength is 460 nm and said third wavelength is 350 nm.

4. The method as claimed in claim 2 wherein said first wavelength is 340 nm, said second wavelength is 480 nm and said third wavelength is 420 nm.

5. The method as claimed in claim 2 wherein said first wavelength is 320 nm, said second wavelength is 460 nm and said third wavelength is 360 nm.

6. The method as claimed in claim 2 wherein the tissue sample is cervical tissue and wherein said first wavelength is 300 nm, said second wavelength is 380 nm and said third wavelength is 340 nm.

7. The method as claimed in claim 2 wherein the tissue sample is cervical tissue and wherein said first wavelength is 340 nm, said second wavelength is 460 and said third wavelength is 380 nm.

8. The method as claimed in claim 2 wherein the tissue sample is human breast tissue and wherein said first wavelength is 340 nm, said second wavelength is 520 nm and said third wavelength is 460 nm.

* * * * *